(12) United States Patent
Zhou (10) Patent No.: US 7,605,004 B2
(45) Date of Patent: *Oct. 20, 2009

(54) TEST STRIP FOR A LATERAL FLOW ASSAY FOR A SAMPLE CONTAINING WHOLE CELLS

(75) Inventor: Siliang Zhou, Hayward, CA (US)

(73) Assignee: Relia Diagnostic Systems LLC, San Francisco, CA (US)

( * ) Notice: Subject to any disclaimer, the term of this patent is extended or adjusted under 35 U.S.C. 154(b) by 515 days.

This patent is subject to a terminal disclaimer.

(21) Appl. No.: 10/200,058

(22) Filed: Jul. 18, 2002

(65) Prior Publication Data

US 2003/0032196 A1    Feb. 13, 2003

Related U.S. Application Data (60) Provisional application No. 60/306,660, filed on Jul. 18, 2001.

(51) Int. Cl.
| | |
|---|---|
| G01N 21/00 | (2006.01) |
| G01N 15/06 | (2006.01) |
| G01N 33/53 | (2006.01) |
| G01N 33/566 | (2006.01) |
| G01N 33/543 | (2006.01) |
| G01N 21/77 | (2006.01) |
| G01N 1/18 | (2006.01) |
| B01L 3/02 | (2006.01) |
| C12Q 1/00 | (2006.01) |
| C12M 1/34 | (2006.01) |
| C12M 3/00 | (2006.01) |

(52) U.S. Cl. .................. 436/518; 422/55; 422/56; 422/57; 422/68.1; 422/101; 435/4; 435/7.1; 435/287.1; 435/287.2; 435/287.7; 435/287.8; 435/287.9; 435/288.3; 435/288.7; 435/970; 436/501; 436/164; 436/169; 436/177; 436/178

(58) Field of Classification Search ............ 422/55, 422/56, 57, 68.1, 101; 435/4, 7.1, 970; 287.1–287.2, 435/287.7, 287.8, 287.9, 288.3, 288.7; 436/501, 436/518, 164, 169, 177, 178

See application file for complete search history.

(56) References Cited

U.S. PATENT DOCUMENTS 4,340,482 A    7/1982   Sternberg (Continued)

FOREIGN PATENT DOCUMENTS

CN    2484568    4/2002

(Continued)

OTHER PUBLICATIONS

Birnbaum, Staffan et al; Latex-Based Thin-Layer Immunoaffinity chromatography for Quantitation of Protein Analytes; Anal. Biochem 206(1) 168-171 (1992); Academic Press Inc. 30 Corporate Dr., Ste. 400, Burlington, MA, United States.

(Continued)

*Primary Examiner*—Bao-Thuy L Nguyen
*Assistant Examiner*—Jacqueline Diramio
(74) *Attorney, Agent, or Firm*—Dennis A. Bennett (57) ABSTRACT

A test strip for conducting a lateral flow assay for detection of an analyte in a sample that contains cells and fluid is provided, as well as methods for making and using the test strip. This test strip is commercially usable, for example, in a diagnostic device at a point of care for detection of analytes in whole blood.

32 Claims, 2 Drawing Sheets

U.S. PATENT DOCUMENTS

| | | | |
|---|---|---|---|
| 4,618,533 | A | 10/1986 | Steuck |
| 4,626,684 | A | 12/1986 | Landa |
| 4,703,017 | A | 10/1987 | Campbell et al. |
| 4,743,560 | A | 5/1988 | Campbell et al. |
| 4,816,224 | A | 3/1989 | Vogel et al. |
| 4,822,566 | A | 4/1989 | Newman |
| 4,943,522 | A | 7/1990 | Eisinger |
| 5,028,535 | A | 7/1991 | Buechler |
| 5,037,736 | A | 8/1991 | Freitag et al. |
| 5,049,487 | A | 9/1991 | Phillips |
| 5,089,391 | A | 2/1992 | Buechler |
| 5,096,837 | A | 3/1992 | Fan |
| 5,211,914 | A | 5/1993 | Vogel et al. |
| 5,232,835 | A | 8/1993 | Litman |
| 5,234,813 | A | 8/1993 | McGeehan et al. |
| 5,238,652 | A | 8/1993 | Sun |
| 5,240,862 | A | 8/1993 | Koenhen et al. |
| 5,266,497 | A | 11/1993 | Imai |
| 5,300,779 | A | 4/1994 | Hillman |
| 5,344,754 | A | 9/1994 | Zweig |
| 5,356,785 | A | 10/1994 | McMahon |
| 5,413,939 | A | 5/1995 | Gustafson |
| 5,418,143 | A | 5/1995 | Zweig |
| 5,458,852 | A | 10/1995 | Beuchler |
| 5,468,648 | A | 11/1995 | Chandler |
| 5,554,531 | A | 9/1996 | Zweig |
| 5,580,794 | A | 12/1996 | Allen |
| 5,589,399 | A | 12/1996 | Allen et al. |
| 5,602,040 | A | 2/1997 | May et al. |
| 5,650,334 | A | 7/1997 | Zuk et al. |
| 5,656,448 | A | 8/1997 | Kang et al. |
| 5,660,993 | A | 8/1997 | Cathey et al. |
| 5,679,526 | A | 10/1997 | Buechler et al. |
| 5,679,579 | A | 10/1997 | Gustafson |
| 5,712,172 | A | 1/1998 | Huang et al. |
| 5,726,010 | A | 3/1998 | Clark |
| 5,750,333 | A | 5/1998 | Clark |
| 5,753,517 | A | 5/1998 | Brooks |
| 5,766,552 | A | 6/1998 | Doshi et al. |
| 5,766,875 | A | 6/1998 | Hafeman et al. |
| 5,821,073 | A | 10/1998 | Lee |
| 5,824,268 | A * | 10/1998 | Bernstein et al. ............. 422/56 |
| 5,922,615 | A | 7/1999 | Nowakowski et al. |
| 5,939,272 | A | 8/1999 | Buechler et al. |
| 5,985,675 | A | 11/1999 | Charm et al. |
| 6,001,658 | A | 12/1999 | Fredrickson |
| 6,007,999 | A | 12/1999 | Clark |
| 6,136,610 | A | 10/2000 | Polito et al. |
| 6,284,194 | B1 | 9/2001 | Chu |
| 6,528,323 | B1 * | 3/2003 | Thayer et al. ............... 436/518 |
| 6,551,842 | B1 * | 4/2003 | Carpenter ................... 436/518 |
| 6,602,719 | B1 * | 8/2003 | Carpenter ................... 435/7.1 |
| 6,617,116 | B2 * | 9/2003 | Guan et al. ................. 436/518 |
| 6,737,278 | B1 * | 5/2004 | Carlsson et al. ............. 436/518 |
| 6,766,817 | B2 | 7/2004 | da Silva |
| 6,767,710 | B2 * | 7/2004 | DiNello et al. ............... 435/7.1 |
| 6,918,404 | B2 | 7/2005 | Dias da Silva |
| 7,066,586 | B2 | 6/2006 | da Silva |
| 7,229,839 | B2 * | 6/2007 | Thayer et al. ............... 436/518 |
| 7,270,995 | B2 * | 9/2007 | Matsushita et al. .......... 436/518 |
| 7,285,255 | B2 | 10/2007 | Kadlec et al. |
| 7,309,611 | B2 * | 12/2007 | DiNello et al. ............. 436/514 |
| 2004/0096356 | A1 * | 5/2004 | Degelaen et al. ............. 422/56 |
| 2007/0283747 | A1 * | 12/2007 | DiNello et al. ............. 73/61.56 |

FOREIGN PATENT DOCUMENTS

| | | |
|---|---|---|
| EP | 322340 | 6/1989 |
| GB | 2204398 | 11/1988 |
| WO | 9113998 | 9/1991 |
| WO | 9212428 | 7/1992 |
| WO | 9303176 | 2/1993 |
| WO | 9607101 | 3/1996 |
| WO | 9622533 | 7/1996 |
| WO | 9707993 | 3/1997 |
| WO | 9708551 | 3/1997 |
| WO | 9737222 | 10/1997 |
| WO | 9827435 | 6/1998 |
| WO | WO 99/18439 A1 | 4/1999 |
| WO | 0058730 | 10/2000 |
| WO | WO 00/62060 | 10/2000 |
| WO | 03008933 | 1/2003 |

OTHER PUBLICATIONS

Fu, Guohui et al; Purification and Characterization of the Human Erythrocyte Band 3 Protein C-terminal Domain; Biochem 43 (6) 1633-1638 (2004) American Chemical Society 1155 16th Street NW Washington, DC 20036.

Goldstein, IJ et al; What should be called a lectin?; Nature, 285 66 (1980); Palgrave Macmillan Ltd., Houndmills, Basingstoke, Hampshire, RG21 6XS, England.

Hayes, Fred et al; Simultaneous Immunoassay Using Electrochemical Detection of Metal Ion Labels; Anal Chem, 66 (11) 1860-1865 (1994); American Chemical Society 1155 16th Street NW Washington, DC 20036.

Klimov, Alex et al; Improved Immunochromatographic Format for Competitive-Type Assays; Clin Chem 41;1360 (1995); American Association for Clinical Chemistry, 1850 K Street, NW Suite 625 Washington, DC 20006.

Holliger, Philip et al; Artificial antibodies and Enzymes: Mimicking Nature and Beyond; Trends Biotech 13 (1) 7-9 (1995); Elsevier Science Ltd, 6277 Sea Harbor Drive Orlando, FL 32887-4800 USA.

Roberts, Matthew et al; Investigation of Liposome-Based Immunomigration Sensors for the Detection of Polychlorinated Biophenyls; Anal Chem. (67) 482-491 (1995); American Chemical Society 1155 16th Street NW Washington, DC 20036.

Chamow, Steven et al; Immunoadhesins: Principles and Applications; Trends Biotech. 14(2) 52-60 (1996); Elsevier Science Ltd, 6277 Sea Harbor Drive Orlando, FL 32887-4800 USA.

Schnebli, H.P. et al; Reaction of Lectins with Human Erythrocytes. I. Factors Governing the Agglutination Reaction; Exp Cell Res. 91 (1) 175-183 (1975); Academic Press Inc. 30 Corporate Dr., Ste. 400, Burlington, MA, United States.

Stephenson, Joanne; RAMP: A Quantitative Immunoassay Platform Takes Shape; IVD Technology 51 (1998); Canon Communications. 11444 W. Olympic Blvd. Los Angeles, CA 90064.

Van Oudheusden, A.P.M. et al; A Multilayer Membrane System for Blood Plasma Isolation for use in Primary Health Care; Ann Clin Biochem. 28 (Pt. 1) 55-59 (1991); Association for Clinical Biochemistry, 130-132 Tooley St, London SE1 2TU.

Wang, Da Neng; Band 3 Protein: Structure, Flexibility and Function; FEBS Letter 346 (1) 26-31 (1994); FEBS Federation of European Biochemical Societies.

Young, Mark et al; Distinct Regions of Human Glycophorin A Enhance Human Red Cell Anion Exchanger (Band 3; AE1) Transport Function and Surface Trafficking; Biol Chem. 278 (35) 32954-61 (2003); American Society for Biochemistry and Molecular Biology, Inc., Bethesda, MD, 20814.

* cited by examiner

TEST STRIP FOR A LATERAL FLOW ASSAY FOR A SAMPLE CONTAINING WHOLE CELLS

CROSS-REFERENCE TO RELATED APPLICATIONS

This application is related to U.S. Provisional Patent Application Ser. No. 60/306,660, entitled "A Test Strip for Lateral Flow Assay for a Sample Containing Whole Cells," filed Jul. 18, 2001, from which priority is claimed under 35 USC §119 (e)(1), and which application is incorporated herein by reference in its entirety.

FIELD OF THE INVENTION

This invention relates to the field of medicine and diagnostics. In particular, the invention relates to lateral flow assay for the detection of an analyte in a sample containing whole cells, such as blood cells in a blood sample.

BACKGROUND OF THE INVENTION

PraxSys BioSystems developed ReLIA Technology, as described in U.S. Pat. No. 6,136,610, the contents of which are incorporated herein by reference in their entireties. The PraxSys device contains a test strip that is not suitable for use when the sample to be analyzed contains whole cells, such as a blood sample containing red blood cells. Therefore, there remains an unmet need for a test strip that can be used for detection of an analyte in a sample containing whole cells.

U.S. Pat. No. 5,240,862, the contents of which are herein incorporated by reference is their entireties, describes blood separation materials. However, this separation methodology requires the use of a separation membrane and a collection membrane in a device, removal of the separation membrane from the collection membrane, and use of the collection membrane for further analysis. This methodology is often cumbersome and is not suitable for use in a lateral flow assay.

Thus, there also remains a need for simpler methods for detection of an analyte in a sample containing whole cells.

SUMMARY OF THE INVENTION

To address the unmet needs and to overcome the disadvantages of the prior art test strip, there is provided herein a test strip that is commercially usable for conducting a lateral flow assay for detection of an analyte in a sample that contains cells and fluid. In certain embodiments, the test strip comprises: (a) a first membrane that comprises a chromatographic strip, where the chromatographic strip comprises a first end and a second end; and (b) a sample filter having an upper surface and a lower surface, where the lower surface of the sample filter is in capillary contact with the chromatographic strip; where the sample filter is capable of separating the cells in the sample from fluid in the sample and allows the fluid to pass through to the chromatographic strip, and where the test strip supports lateral flow of the fluid from the sample filter towards the second end of the chromatographic strip.

There is provided in another embodiment of the present invention, a test strip as described herein, where the sample that can be analyzed is a sample of body fluids. In further embodiments of the present invention, the sample is a blood sample, a saliva sample, a urine sample, sample taken from lymphatic tissues, a sample from a spinal tap, or a sample taken from a peritoneal cavity, synovial fluid from a joint, or fluid from lungs.

In a further embodiment of the present invention, there is provided the test strip, as above, where the sample filter comprises a surface that contacts the sample and the surface is hydrophilic.

In as yet another embodiment of the present invention, there is provided a test strip for conducting a lateral flow assay for detection of an analyte in a sample that contains cells and fluid, where the test strip comprises: (a) a first membrane that comprises a chromatographic strip, where the chromatographic strip comprises a first end and a second end; and (b) a sample filter having an upper surface and a lower surface, where the lower surface of the sample filter is in capillary contact with the chromatographic strip and where the sample filter comprises pores of varying pore sizes to allow the cells from the sample to be retained in the sample filter and the fluid in the sample to pass through the sample filter; and where the test strip supports lateral flow of fluid in the sample from the sample filter towards the second end of the chromatographic strip.

There is further provided in another embodiment of the present invention, a test strip for conducting a lateral flow assay for detection of an analyte in a sample that contains cells and fluid, where the test strip comprises: (a) a first membrane that comprises a chromatographic strip, where the chromatographic strip comprises a first end and a second end; and (b) a sample filter having an upper surface and a lower surface, and first and second pores, where the lower surface of the sample filter is in capillary contact with the chromatographic strip, the first pores are closer to the upper surface of the sample filter and the second pores are closer to the lower surface of the sample filter, the first pores comprising a first pore size and the second pores having a second pore size, and where the first pore size is larger than the second pore size, the sample filter allows the cells from the sample to be retained in the sample filter and the fluid in the sample to pass through the sample filter; and where the test strip supports lateral flow of fluid in the sample from the sample filter towards the second end of the chromatographic strip.

In as yet another embodiment of the present invention, there is provided a test strip for conducting a lateral flow assay for detection of an analyte in a sample that contains red blood cells, where the test strip comprises: (a) a first membrane that comprises a chromatographic strip, where the chromatographic strip comprises a first end and a second end; and (b) a sample filter having an upper surface and a lower surface, where the lower surface of the sample filter is in capillary contact with the chromatographic strip; and where the sample filter is capable of separating the red blood cells in the sample from fluid in the sample, and allows the fluid to pass through to the chromatographic strip, and the test strip supports lateral flow of the fluid from the sample filter towards the second end of the chromatographic strip.

There is provided in as yet another embodiment of the present invention, a test strip for conducting a lateral flow assay for detection of an analyte in a sample that contains red blood cells, where the test strip comprises: (a) a first membrane that comprises a chromatographic strip, where the chromatographic strip comprises a first end and a second end; and (b) a sample filter having an upper surface and a lower surface, where the lower surface of the sample filter is in capillary contact with the chromatographic strip and where the sample filter comprises pores of varying pore sizes to allow the red blood cells from the sample to be retained in the sample filter and the fluid in the sample to pass through the sample filter; and where the test strip supports lateral flow of fluid in the sample from the sample filter towards the second end of the chromatographic strip.

There is additionally provided in another embodiment of the present invention, a test strip for conducting a lateral flow assay for detection of an analyte in a sample that contains red blood cells, where the test strip comprises: (a) a first membrane that comprises a chromatographic strip, where the chromatographic strip comprises a first end and a second end; and (b) a sample filter having an upper surface and a lower surface and first and second pores, where the lower surface of the sample filter is in capillary contact with the chromatographic strip, the first pores are closer to the upper surface of the sample filter and the second pores are closer to the lower surface of the sample filter, the first pores comprising a first pore size and the second pores comprising a second pore size, and where the first pore size is larger than the second pore size, the sample filter allows the cells from the sample to be retained in the sample filter and the fluid in the sample to pass through the sample filter; and where the test strip supports lateral flow of fluid in the sample from the sample filter towards the second end of the chromatographic strip.

In still another embodiment of the present invention, there is provided a test strip for conducting a lateral flow assay for detection of an analyte in a sample that contains cells and fluid, where the test strip comprises: (a) a first membrane that comprises a chromatographic strip, where the chromatographic strip comprises a first end and a second end; (b) a sample pad situated close to the first end of the chromatographic strip, where the sample pad comprises an upper surface and a lower surface, and the lower surface of the sample pad is in capillary contact with the chromatographic strip; and (c) a sample filter comprising an upper surface and a lower surface, where the lower surface of the sample filter is in capillary contact with the upper surface of the sample pad; and where the sample filter is capable of separating the cells in the sample from fluid in the sample and allows the fluid to pass through, the sample pad also allows the fluid to pass through to the chromatographic strip, and the test strip supports lateral flow of fluid in the sample from the sample pad towards the second end of the chromatographic strip.

There is provided in another embodiment of the present invention, a test strip as described herein, where the sample is a blood sample and the cells are blood cells.

There is additionally provided in another embodiment of the present invention a test strip for conducting a lateral flow assay for detection of an analyte in a sample that contains cells and fluid, where the test strip comprises: (a) a first membrane that comprises a chromatographic strip, where the chromatographic strip comprises a first end and a second end; (b) a sample pad situated close to the first end of the chromatographic strip, where the sample pad comprises an upper surface and a lower surface, and the lower surface of the sample pad is in capillary contact with the chromatographic strip; and (c) a sample filter comprising an upper surface and a lower surface, where the lower surface of the sample filter is in capillary contact with the upper surface of the sample pad, and where the sample filter comprises pores of varying pore sizes to allow the cells from the sample to be retained in the sample filter and the fluid in the sample to pass through the sample filter; and where the test strip supports lateral flow of fluid in the sample from the sample pad towards the second end of the chromatographic strip.

There is additionally provided in another embodiment of the present invention a test strip for conducting a lateral flow assay for detection of an analyte in a sample that contains cells and fluid, where the test strip comprises: (a) a first membrane that comprises a chromatographic strip, where the chromatographic strip comprises a first end and a second end; (b) a sample pad situated close to the first end of the chromatographic strip, where the sample pad comprises an upper surface and a lower surface, and the lower surface of the sample pad is in capillary contact with the chromatographic strip; and (c) a sample filter comprising an upper surface and a lower surface and first and second pores, where the lower surface of the sample filter is in capillary contact with the upper surface of the sample pad, the first pores are closer to the upper surface of the sample filter and the second pores are closer to the lower surface of the sample filter, the first pores comprising a first pore size and the second pores comprising a second pore size, and where the first pore size is larger than the second pore size, the sample filter allows the cells from the sample to be retained in the sample filter and the fluid in the sample to pass through the sample filter; and where the test strip supports lateral flow of fluid in the sample from the sample pad towards the second end of the chromatographic strip.

In as yet another embodiment of the present invention, there is provided a test strip as described herein, further comprising a selective membrane, where the selective membrane is positioned under the sample filter. In an embodiment of the present invention, there is provided the selective membrane, which lies on top of the sample pad. In another embodiment of the present invention, the selective membrane lies on top of the chromatographic strip. In any event, the selective membrane is in capillary contact with the sample filter and the sample pad or the chromatographic strip to allow fluid to pass through the selective membrane under capillary or osmotic forces. The selective membrane contains an agent that can selectively bind to a component in the sample to effectively remove the component from the assay environment.

There is further provided, in another embodiment of the present invention, one or more other filters or membranes between the sample filter and the chromatographic strip for one or more purposes, provided that the additional one or more membranes do not impair the capillary or osmotic flow of fluid from the sample filter to the chromatographic strip, and provided that the height of the combined filters or membranes does not impair the ability of the test strip to be fitted in a cassette to be read in an instrument.

In an embodiment of the present invention, the selective membrane contains an agent that is an antibody, an antigen, a metabolite, a hormone, an enzyme, a virus, a prion, or parts thereof, or an agent that binds to such.

In as yet another embodiment of the present invention, there is provided a test strip for conducting a lateral flow assay for detection of an analyte in a sample that contains blood cells, where the test strip comprises: (a) a first membrane that comprises a chromatographic strip, where the chromatographic strip comprises a first end and a second end; (b) a sample pad situated close to the first end of the chromatographic strip, where the sample pad comprises an upper surface and a lower surface, and the lower surface of the sample pad is in capillary contact with the chromatographic strip; and (c) a sample filter comprising an upper surface and a lower surface, where the lower surface of the sample filter is in capillary contact with the upper surface of the sample pad, and where the sample filter is capable of separating the red blood cells in the sample from fluid in the sample and allows the fluid to pass through, the sample pad also allows the fluid to pass through to the chromatographic strip, and the test strip supports lateral flow of fluid in the sample from the sample pad towards the second end of the chromatographic strip.

There is also provided in a further embodiment of the present invention, a test strip as described herein, where the sample pad comprises a surface that contacts the fluid, and the surface is hydrophilic.

There is further provided in another embodiment of the present invention, a test strip for conducting a lateral flow assay for detection of an analyte in a sample that contains red blood cells, where the test strip comprises: (a) a first membrane that comprises a chromatographic strip, where the chromatographic strip comprises a first end and a second end; (b) a sample pad situated close to the first end of the chromatographic strip, where the sample pad comprises an upper surface and a lower surface, and the lower surface of the sample pad is in capillary contact with the chromatographic strip; and (c) a sample filter comprising an upper surface and a lower surface, where the lower surface of the sample filter is in capillary contact with the upper surface of the sample pad, and where the sample filter comprises pores of varying pore sizes to allow the red blood cells from the sample to be retained in the sample filter and the fluid in the sample to pass through the sample filter; and where the test strip supports lateral flow of fluid in the sample from the sample pad towards the second end of the chromatographic strip.

In as yet another embodiment of the present invention, there is provided a test strip for conducting a lateral flow assay for detection of an analyte in a sample that contains blood cells, where the test strip comprises: (a) a first membrane that comprises a chromatographic strip, where the chromatographic strip comprises a first end and a second end; (b) a sample pad situated close to the first end of the chromatographic strip, where the sample pad comprises an upper surface and a lower surface, and the lower surface of the sample pad is in capillary contact with the chromatographic strip; and (c) a sample filter comprising an upper surface and a lower surface and first and second pores, where the lower surface of the sample filter is in capillary contact with the upper surface of the sample pad, the first pores are closer to the upper surface of the sample filter and the second pores are closer to the lower surface of the sample filter, the first pores comprising a first pore size and the second pores comprising a second pore size, and where the first pore size is larger than the second pore size, the sample filter allows the red blood cells from the sample to be retained in the sample filter and the fluid in the sample to pass through the sample filter; and where the test strip supports lateral flow of fluid in the sample from the sample pad towards the second end of the chromatographic strip.

Further, there is provided in another embodiment of the present invention, a test strip for conducting a lateral flow assay for detection of an analyte in a sample that contains cells and fluid, where the test strip comprises: (a) a first membrane that comprises a chromatographic strip, where the chromatographic strip comprises a first end and a second end; (b) a sample pad situated close to the first end of the chromatographic strip, where the sample pad comprises an upper surface and a lower surface, and the lower surface of the sample pad is in capillary contact with the chromatographic strip; (c) a sample filter comprising an upper surface and a lower surface, where the lower surface of the sample filter is in capillary contact with the upper surface of the sample pad; (d) a conjugate pad situated at or close to the second end of the chromatographic strip, where the conjugate pad comprises an upper surface and a lower surface, and the lower surface of the conjugate pad is in capillary contact with the chromatographic strip; (e) a reagent pad comprising an upper surface and a lower surface, where the lower surface of the reagent pad is in capillary contact with the upper surface of the conjugate pad; and (f) an absorbent pad situated at the first end of the chromatographic strip and to a side of the sample pad that is away from the conjugate pad, where the absorbent pad is in capillary contact with the chromatographic strip; and where the sample filter is capable of separating the cells from the fluid in the sample and the test strip supports lateral flow of fluid in the sample from the sample pad towards the conjugate pad.

Moreover, there is provided in one embodiment of the present invention, the test strip as described herein, where reagent pad is suitable for application of a reagent, such as a buffer, to release the conjugate from the conjugate pad.

In a further embodiment of the present invention, there is provided a reagent pad that may be the same or different from the sample filter. Where the reagent pad is the same as the sample filter, a sample can be applied to the reagent pad to release the conjugate from the conjugate pad, but only if the sample does not react with the conjugate to form any complexes that would impair the capillary or osmotic flow of the fluid onto the chromatographic strip for conduct of the assay.

In another embodiment of the present invention, there is provided a test strip for conducting a lateral flow assay for detection of an analyte in a sample that contains whole cells and fluid, where the test strip comprises: (a) a first membrane that comprises a chromatographic strip, where the chromatographic strip comprises a first end and a second end; (b) a sample pad situated at the first end of the chromatographic strip, where the sample pad comprises an upper surface and a lower surface, and the lower surface of the sample pad is in capillary contact with the chromatographic strip; (c) a sample filter comprising an upper surface and a lower surface, where the lower surface of the sample filter is in capillary contact with the upper surface of the sample pad and where the sample filter comprises varying pore sizes and allows the cells to be retained in the sample filter and the fluid to pass through the sample filter; (d) a conjugate pad situated at the second end of the chromatographic strip, where the conjugate pad comprises an upper surface and a lower surface, and the lower surface of the conjugate pad is in capillary contact with at least a portion of the chromatographic strip; (e) a reagent pad comprising an upper surface and a lower surface, where the lower surface of the reagent pad is in capillary contact with the upper surface of the conjugate pad; and (f) an absorbent pad situated at the first end of the chromatographic strip and to a side of the sample pad that is away from the conjugate pad, where the absorbent pad is in capillary contact with the chromatographic strip; and where the test strip supports lateral flow of fluid in the sample from the sample pad towards the conjugate pad.

Moreover, in another embodiment of the present invention, there is provided a test strip for conducting a lateral flow assay for detection of an analyte in a sample that contains whole cells and fluid, where the test strip comprises: (a) a first membrane that comprises a chromatographic strip, where the chromatographic strip comprises a first end and a second end; (b) a sample pad situated at the first end of the chromatographic strip, where the sample pad comprises an upper surface and a lower surface, and the lower surface of the sample pad is in capillary contact with the chromatographic strip; (c) a sample filter comprising an upper surface and a lower surface and first and second pores, where the lower surface of the sample filter is in capillary contact with the upper surface of the sample pad, the first pores are closer to the upper surface of the sample filter and the second pores are closer to the lower surface of the sample filter, the first pores comprising a first pore size and the second pores comprising a second pore size, and where the first pore size is larger than the second pores size, the sample filter allows the cells to be retained in the sample filter and the fluid to pass through the sample filter; (d) a conjugate pad situated at the second end of the chromatographic strip, where the conjugate pad comprises an upper surface and a lower surface, and the lower surface of the conjugate pad is in capillary contact with at least a portion of the chromatographic strip; (e) a reagent pad comprising an upper surface and a lower surface, where the lower surface of the reagent pad is in capillary contact with the upper surface of the conjugate pad; and (f) an absorbent pad situated at the first end of the chromatographic strip and to a side of the sample pad that is away from the conjugate pad, where the absorbent pad is in capillary contact with the chromatographic strip; and where the test strip supports lateral flow of fluid in the sample from the sample pad towards the conjugate pad.

There is additionally provided in another embodiment of the present invention, a test strip for conducting a lateral flow assay for detection of an analyte in a sample that contains blood cells and fluid, where the test strip comprises: (a) a first membrane that comprises a chromatographic strip, where the chromatographic strip comprises a first end and a second end; (b) a sample pad situated at the first end of the chromatographic strip, where the sample pad comprises an upper surface and a lower surface, and the lower surface of the sample pad is in capillary contact with the chromatographic strip; (c) a sample filter comprising an upper surface and a lower surface, where the lower surface of the sample filter is in capillary contact with the upper surface of the sample pad and the sample filter is capable of separating red blood cells from fluid in the sample; (d) a conjugate pad situated at the second end of the chromatographic strip, where the conjugate pad comprises an upper surface and a lower surface, and the lower surface of the conjugate pad is in capillary contact with at least a portion of the chromatographic strip; (e) a reagent pad comprising an upper surface and a lower surface, where the lower surface of the reagent pad is in capillary contact with the upper surface of the conjugate pad; and (f) an absorbent pad situated at the first end of the chromatographic strip and to a side of the sample pad that is away from the conjugate pad, where the absorbent pad is in capillary contact with the chromatographic strip; and where the test strip is capable of supporting lateral flow of fluid in the sample from the sample pad towards the conjugate pad.

There is additionally provided in another embodiment of the present invention, a test strip as described herein, further comprising: (d) a conjugate pad situated between the sample pad and the second end of the chromatographic strip, where the conjugate pad comprises an upper surface and a lower surface, and the lower surface of the conjugate pad is in capillary contact with the chromatographic strip; and (f) an absorbent pad situated at the second end of the chromatographic strip, where the absorbent pad is in capillary contact with the chromatographic strip; and where the test strip is capable of supporting lateral flow of fluid in the sample from the sample pad towards the conjugate pad.

There is further provided in another embodiment of the present invention, a test strip as described herein adapted for conduct of an immunoassay on the chromatographic strip for detection of an analyte in a sample containing cells and fluid. In an aspect of the present embodiment, the test strip comprises a conjugate that can be released from the conjugate pad upon application of fluid to the conjugate pad, where the conjugate is capable of combining with the analyte to be detected to form a detectable signal, indicating the presence of the analyte. In another aspect of the present invention, the conjugate comprises a first binding agent that is capable of binding to the analyte. Examples of the first binding agent include an antibody and an antigen, if the analyte is an antibody. In a further aspect of the present embodiment, the conjugate comprises a second binding agent, where the second binding agent comprises a detectable marker and binds either to the first binding agent or to the analyte.

In a further embodiment of the present invention, the detectable signal can be quantified. In such an instance, the immunoassay of the present invention is a quantitative immunoassay.

In yet another embodiment of the present invention, there is provided a test strip as described herein, where the chromatographic strip supports the capillary flow of fluid from the sample filter situated close to the first end of the chromatographic strip to the second end of the chromatographic strip, and the capillary flow of conjugate, released from the conjugate pad, from the second end of the chromatographic strip towards the first end of the chromatographic strip, allowing the conjugate to come into contact with the fluid from the sample to form an immobilized complex, and allowing the detection of the complex.

There is also provided in yet another embodiment of the present invention, a test strip as described herein, where the conjugate pad is situated in any appropriate location on the chromatographic strip to allow and facilitate the conduct of the immunoassay.

In yet another embodiment of the present invention, there is provided a conjugate pad that is situated between the sample filter and the second end of the chromatographic strip, and the chromatographic strip supports the flow of fluid from the sample filter to the conjugate pad to release the conjugate.

In a further embodiment of the present invention, there is provided a conjugate pad that is situation under the sample filter and is in capillary contact with the sample filter and the chromatographic strip and allows the flow of fluid from the sample filter through the conjugate pad to the chromatographic strip.

There is also provided in one embodiment of the present invention, a chromatographic strip that comprises a chromatographic membrane, an adhesive layer and a backing for the adhesive layer.

In an embodiment of the present invention, there is provided a chromatographic membrane that is made of nitrocellulose.

In yet another embodiment of the present invention, there is provided a sample filter that is a blood cell/plasma separation membrane encoded S/G available from Spectral Diagnostics Inc.

There is further provided in another embodiment of the present invention, a method of making a test strip for conducting a lateral flow assay for detection of an analyte in a sample that contains cells and fluid, comprising the steps of: (a) providing a chromatographic strip having a first end and a second end; and (b) providing a sample filter that comprises an upper and a lower surface close to the first end of the chromatographic strip, where the lower surface of the sample filter is in capillary contact with the chromatographic strip to allow flow of fluid capillary contact between the sample filter and the chromatographic strip, where the test strip supports lateral flow of fluid from the sample filter to the second end of the chromatographic strip.

There is additionally provided in another embodiment of the present invention, the method of making a test strip as described herein, further comprising the step of: (c) placing a sample pad between the sample filter and the chromatographic strip, where the sample pad is in capillary contact with the sample filter and the chromatographic strip, and fluid can flow from the sample filter through the sample pad to the chromatographic strip by capillary or osmotic forces.

There is further provided in another embodiment of the present invention, the method of making a test strip as described herein, further comprising the step of: (d) providing a conjugate pad on the chromatographic strip, where the conjugate pad is in capillary contact with the chromatographic strip, and fluid can flow through the conjugate pad to the chromatographic strip by capillary or osmotic forces.

There is additionally provided in another embodiment of the present invention, the method of making a test strip as described herein, further comprising the step of (e) providing a reagent pad on the conjugate pad, where the reagent pad is in capillary contact with the conjugate pad and allows the flow of fluid from the reagent pad to the conjugate pad.

In a further embodiment of the present invention, there is provided the method of making a test strip as described herein, further comprising the step of (f) providing a selective membrane between the sample filter and the chromatographic strip, where the selective membrane is in capillary contact with the sample filter and the chromatographic strip and allows the flow of fluid from the sample filter to the chromatographic strip.

There is also provided in another embodiment of the present invention, a method of separating cells from fluid in a sample for conduct of a lateral flow assay for detection of an analyte in the sample, comprising the steps of: (a) providing a test strip as described herein; and (b) applying the sample on the sample filter.

There is further provided in another embodiment of the present invention, a method of conducting a lateral flow assay for detection of an analyte in a sample that contains cells and fluid, comprising the steps of: (a) providing a test strip as described herein; (b) applying the sample on the sample filter; (c) allowing flow of fluid from the sample filter to the chromatographic strip and towards the second end of the chromatographic strip; (d) applying a buffer to release the conjugate in the conjugate pad; (e) allowing flow of the conjugate towards the analyte in the sample to form a complex; and (f) detecting presence of the complex.

There is additionally provided, in another embodiment of the present invention, a method of conducting a lateral flow assay as above, further comprising the step of: (g) quantifying amount of complex formed.

These and other aspects and embodiments of the invention will become evident upon reference to the following detailed description, attached figures and various references set forth herein that describe in more detail certain procedures or compositions.

DETAILED DESCRIPTION OF THE INVENTION

It has been discovered that the test strip of the present invention can efficiently and effectively separate whole cells from fluid in a sample and can be used to detect an analyte in the sample qualitatively and quantitatively. The test strip of the present invention is commercially usable as a point of care diagnostic (e.g., in a doctor's office or clinic) device. The devices and methods described herein are useful, for example, for the detection of infectious agents, including HIV and HCV as well as other molecules including, for example, deoxypyrodinoline, human serum albumin, drugs of abuse, protein markers such as prostate specific antigen, kidney disease proteins such as lactate dehydrogenate, N-acetyl-β-D-glucosamine, pregnancy or fertility associated hormones such as human chorionic gonadotropin and markers of urinary tract infection. The determination of blood borne analytes such as therapeutic drugs, hormones, cancer markers such as prostate specific antigen, cardiac markers (Troponin I, Troponin T, CKMB) and α-fetoprotein is particularly suited to the present invention. In addition, the sample may be, for example, whole blood. Thus, although the devices and methods of the present invention is suitable for assaying various body fluids such as urine, saliva, sweat or mucous for the presence of particular analytes, it is particularly suitable for assays in which blood is the test fluid including, for example, a small sample volume when the blood is collected by means such as a finger stick.

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, for example, reference to "a sample filter" includes one or more sample filters.

Reference is made herein to various exemplary figures and methods. It is to be understood that the components of the devices described herein may be configured differently or that different combinations of the components may be used. Similarly, it is to be understood that the order of the steps of the methods may be varied from these examples.

Figure 1:
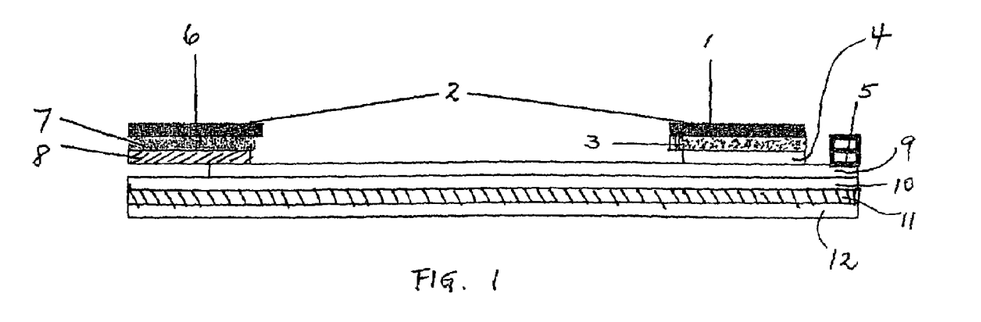
FIG. 1 is a side view of one embodiment of the test strip of the present invention.

Referring to the drawings, FIG. 1 is a side view of one embodiment of the test strip of the present invention. Port I (1) is for application of sample onto sample filter (2), which lies on top of sample pad (3) and, optionally, an additional membrane (4) which may be a selective membrane. The sample filter can be made of any suitable material, for example, a hydrophobic material capable of filtering cells (e.g., blood cells) from fluids. Commercially available filters or membranes can be adapted for use in the devices and methods as described herein, for example filters such as glass microfiber filters (Whatman, Kent, UK or Millipore), PlasmaSep® (Whatman) and/or C/S membrane, C/Q membranes, S/G membranes and others available from Spectral Diagnostics. In a preferred embodiment, the sample filter comprises one or more S/G membranes from Spectral Diagnostics USA, Whitestone, Va., USA. Selection of a sample filter can be made using the teachings described herein, for example to achieve the desired flow rate and/or separation capabilities. The sample application zone can be either hydrophobic or hydrophilic material. In certain embodiments, the sample application zone is hydrophilic to facilitate absorption of the sample into the test strip system. More than one sample filter may be used in any of the devices described herein.

The selective membrane (4) may sit on a chromatographic strip (9), which is optionally supported by a multi-layered backing pad (10) that may contain an adhesive layer (11) and a plastic backing (12) for the adhesive layer (11). Typically, the backing is a hydrophobic, non-porous material such as polystyrene, polyethylene, polypropylene or other nonbibulous hydrophobic material upon which are placed the absorbent portions of the device. Non-limiting examples of suitable hydrophobic materials include polytetrafluoroethylene and materials that are surface treated with hydrophobic materials such as perfluoroethylene and silanizing agents.

Also shown in FIG. 1, is an absorbent pad (5). Absorbent pad (5) is close to Port I (1) and preferably sits on the chromatographic strip (9). The absorbent pad is preferably hydrophilic and can be derived from any number of materials, including but not limited to cellulose, desiccant treated cellulose and surfactant treated porous polymers. Commercially available materials, such as those available from Whatman, may be used in the devices and methods described herein.

At the other end of the chromatographic strip (9) is Port II (6) for application of either sample or a reagent such as a buffer onto the sample filter (2). A buffer pad (7) is generally placed between the sample filter (2) above and a conjugate pad (8) below. The conjugate pad (8) is preferably in capillary contact with the chromatographic strip (9).

Figure 2:
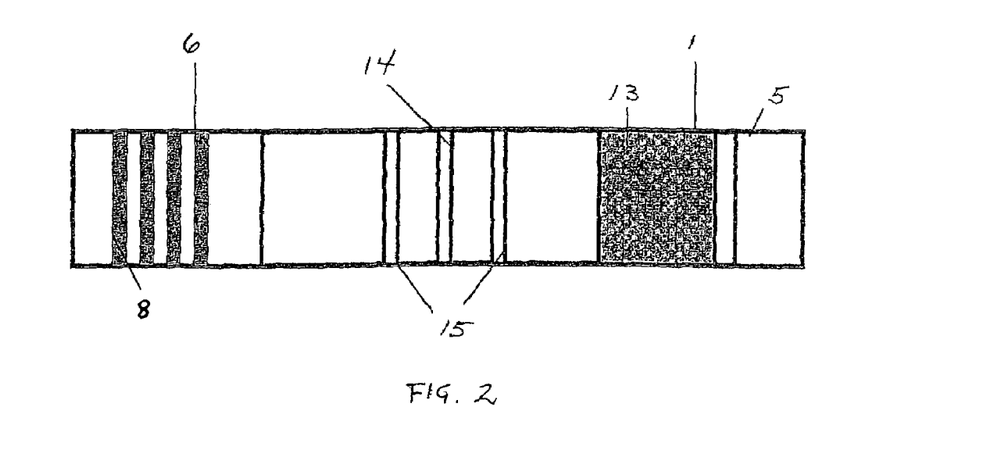
FIG. 2 is a top view of one embodiment of the test strip of the present invention showing placements of the components of an immunoassay for detection of an analyte in a sample.

FIG. 2 is a top view of one embodiment of the test strip of the present invention showing placement of the components of an exemplary immunoassay for detection of an analyte in a sample. Shown in FIG. 2 from right to left are: absorbent pad (5); Port I (1) where a sample (13) is preferably placed; a capture band (14) for capturing the analyte in the sample, on one or both sides of which are optionally control lines (15), for example for the placement of control binding agents. To the left of the control lines (15) is Port II (6) and the conjugate pad (8) containing, for example, gold conjugated antibody or antigen.

The conjugate pad may be hydrophobic or hydrophilic, for example an absorbent, porous material such as glass fiber, polyester or other woven or non-woven synthetic material through which the fluid test sample can flow and may contain one or more mobile conjugate of one or more labeled specific binding partners. The specific binding partner, for example an antibody, can be labeled with detectable label such as, for example, an enzyme, fluorofor, radio active isotope or a direct particulate label such as gold particles or colored latex particles.

Figure 3:
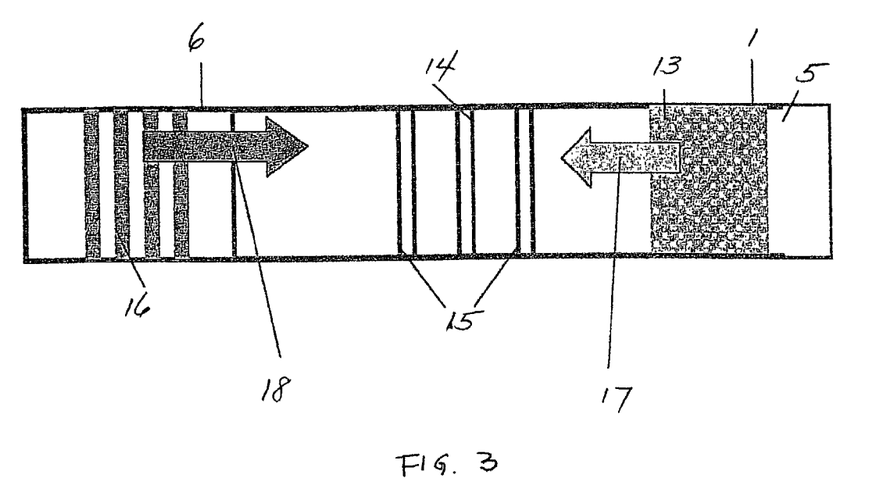
FIG. 3 is a top view of one embodiment of the test strip of the present invention showing the lateral flow of fluid.

FIG. 3 is a top view of one exemplary embodiment of a test strip according to the present invention showing the direction (17) of the lateral flow of fluid from the sample (13) and the direction (18) of the lateral flow of the conjugate (16) from the conjugate pad (8).

Figure 4:
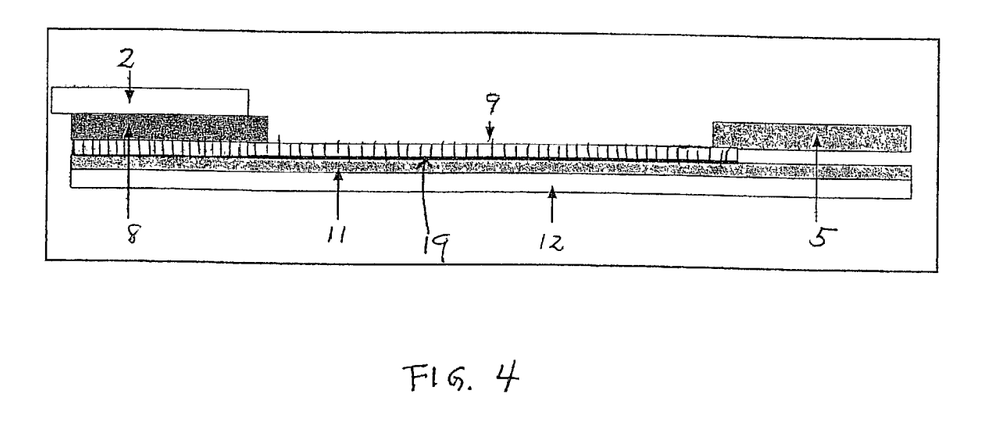
FIG. 4 is a side view of another embodiment of the test strip of the present invention.

FIG. 4 is a side view of another embodiment of the test strip of the present invention. In this embodiment, a sample filter (2) is shown placed over the conjugate pad (8), and the conjugate pad (8) is shown placed over the chromatographic strip (9), which optionally may have a backing (19), and adhesive layer (11) and a plastic backing (12) for the adhesive layer (11). The absorbent pad (5) is shown placed at the opposite end of the chromatographic strip (9).

The overall size of the test strips described herein and the components making up the test strip can vary greatly. In certain embodiments, the chromatographic strip is between about 0.1 cm and 5 cm in length (or any value therebetween), preferably between about 0.5 cm and 2.5 cm (or any value therebetween), and even more preferably about 1 cm in length. As will be apparent, the components of the strip will be sized accordingly, for example, in a 1 cm chromatographic strip, the sample filter can be between about 5 to 10 mm in width (or any value therebetween) and 10 to 20 mm in length (or any value therebetween).

Methods of making such test strips are described herein (see, e.g., Examples) below, in available references and references cited herein. For example, any of the test strips described herein can be made by providing a chromatographic strip having a first end and a second end; and providing a sample filter having an upper surface and a lower surface, such that the lower surface of the sample filter is in capillary contact with the chromatographic strip and the sample filter is (i) capable of separating cells in a sample from fluid in the sample; (ii) allows the fluid to pass through to the chromatographic strip and (iii) facilitates lateral flow of fluid towards the second end of the chromatographic strip. When present, a sample pad can be placed, for example, between the sample filter and the chromatographic strip, preferably such that the sample pad is in capillary contact with the sample filter and the chromatographic strip, and fluid flows from the sample filter through the sample pad to the chromatographic strip by capillary or osmotic forces. Similarly, a conjugate pad may also be provided, generally on the chromatographic strip, such that the conjugate pad is in capillary contact with the chromatographic strip, and fluid flows through the conjugate pad to the chromatographic strip by capillary or osmotic forces. A reagent pad may also be provided, for example, on the conjugate pad, such that the reagent pad is in capillary contact with the conjugate pad and allows the flow of fluid from the reagent pad to the conjugate pad. Further, a selective membrane may be provided, for example between the sample filter and the chromatographic strip, such that the selective membrane is in capillary contact with the sample filter and the chromatographic strip and allows the flow of fluid from the sample filter to the chromatographic strip.

Also described herein are methods of using the test strips, for example to separate cells from fluid in a sample for conduct of a lateral flow assay for detection of an analyte in the sample. Typically, a sample (e.g., one containing fluid and cells) is applied to any of the test strips described herein and the strip separates the cells from the fluid in the sample, for instance by allowing the flow of fluid from the sample filter to the chromatographic strip and towards the second end of the chromatographic strip; applying a buffer to release the conjugate in the conjugate pad; allowing the flow of the conjugate towards the analyte in the sample to form a complex; and detecting presence of the complex. In certain embodiments, quantifying amount of complex formed.

Thus, the lateral flow assay of the present invention can be performed, for example, as follows:

(1) Serum or plasma is obtained from a blood sample added into Port 1, by application of the sample to the sample filter. This membrane typically contains pores (e.g., about 5 microns or less) that allow liquid to pass through, while retaining blood cells (e.g., about 6 microns), either directly onto the chromatographic strip or through a sample pad. As noted above, the membrane is preferably an S/G membrane (Spectral Diagnostics).

(2) Serum or plasma specimen flow towards the reaction region (capture lane and control lines) with pre-coated chemicals.

(3) Antigen or antibody in specimen react with corresponding reagents in reaction region (capture lane and control lines), form immuno-complex 1.

(4) Conjugate release buffer or sample (in some tests) is added to Port-2. the liquid (buffer or sample) will resolve the gold conjugated reagents (antigen or antibody), the reagents then flow towards the reaction region (capture lane and control lines) and react with immuno-complex 1. The colorful bands will be formed in control bands, and capture bands region, if the specimen is positive for the tested item.

(5) The absorbent located in the end near to Port 1 will absorb the excessive liquid that was not absorbed by the chromatographic strip.

The following examples are given by way of illustration to facilitate a better understanding of the invention and are not intended to limit the invention in any way.

EXAMPLE 1

In this example, the chromatographic strip is a nitrocellulose immunochromatographic test strip from Millipore Corporation (http://www.millipore.com; tech service@millipore.com). This test strip was built into the cartridge described in U.S. Pat. No. 6,136,610 ("the '610 patent), issued on Oct. 24, 2000 to assignee PraxSys BioSystems, Inc., and entitled "Method and apparatus for performing a lateral flow assay," the contents of which are incorporated herein by reference in their entireties, including those materials that are incorporated by reference into the '610 patent. The double adhesive tap was made of polyester and was obtained from G& L Precision Cutting. The backing pad was made of plastic and was obtained from G&L Precision Cutting.

The sample filter was made of a blood cell/plasma separation membrane S/G. This sample filter was obtained from Spectral Diagnostics Inc. (135-2 The West Mall, Toronto, Ontario M9C 1C2, Canada), and has been described in van Oudheusden, A. P. M. and Roesink, H. D. W., *Ann. Clin. Biochem.* 28:55-59 (1991), the contents of which are incorporated herein by reference in their entireties; and U.S. Pat. No. 5,240,862 ("the '862 patent"), issued Aug. 31, 1993 to assignee X-Flor B. V. and Primecare B. V., entitled "Process and device for the separation of a body fluid from particulate materials," the contents of which are also incorporated herein by reference in their entireties, including those materials incorporated by reference into the '862 patent.

Other components used are conventional in the industry and can be ordered from any suitable vendor. For example, colloidal gold can be ordered from British BioCell International (Golden Gate, Ty Glas Avenue, Cardiff CF4 5DX, Wales, United Kingdom).

The sample pad and buffer pad were made of a hydrophilic material, Cytosep, which was obtained from Pall Specialty Materials.

The conjugate pad was made from conjugate release pads, a glass, hydrophobic material made by Whatman Inc. (401 West Morgan road, Ann Arbor, Mich. 48108-9109, U.S.A.) and obtained from Pall Specialty materials.

The absorbent was made of a hydrophilic material obtained from Whatman Inc.

EXAMPLE 2

In this example, the sample filter of Example 1 and the conjugate pad, respectively, was each placed directly on top of the nitrocellulose chromatographic membrane, and another sample filter was placed directly on the conjugate pad, all in a configuration as shown in FIG. 1 but without the intervening sample pad, selective membrane, and buffer pad. In this configuration, whole blood was applied to the sample filter in both positions, and the assay was allowed to run its course. Plasma or serum separation was similarly effective and efficient, with the sample fluid flowing into the reaction region, that is, the capture line, in about 90 to 150 seconds, for a chromatographic strip that is 1 cm in length.

EXAMPLE 3

In this example, a sample pad was added under the sample filter and a buffer release pad was added above the conjugate pad. Plasma or serum separation was similarly effective and efficient, with the sample fluid flowing into the reaction region, that is, the capture line, in about 90 to 150 seconds, for a chromatographic strip that is 1 cm in length.

EXAMPLE 4

In this example, blood samples, with or without anti-coagulant reagents were applied on the sample filter of Example 1. Plasma or serum separation was similarly effective and efficient, with the sample fluid flowing into the reaction region, that is, the capture line, in about 90 to 150 seconds, for a chromatographic strip that is 1 cm in length. When blood sample did not contain anti-coagulant, it was not necessary to pre-treat the sample filter with anti-coagulant. In fact, pre-treatment of sample filter with anti-coagulant damaged the sample filter, causing leakage of blood cells.

EXAMPLE 5

In this example, the use of a single layer of sample filter was compared with the use of 2 layers of sample filters. The use of a single layer of sample filter was found to produce a faster flow rate than the use of two sample filters together.

EXAMPLE 6

In this example, the size of the sample filter was varied to optimize the flow rate. For a sample of 50 to 150 microliter of blood sample, the optimal size found was 7 mm (width) by 13 mm (length). Relatively, the larger the size of the sample filter, the shorter the flow time.

EXAMPLE 7

In this example, buffer (50 to 150 microliter) was added about 30 to 60 seconds after a blood sample was applied to the sample filter. The flow time, that is, the time from application of sample to time for fluid to reach the capture line, decreased and the background signal was reduced.

EXAMPLE 8

Anti-HIV testing. An EIA anti-HIV assay confirmed patient blood specimen was collected with anticoagulant reagent. The plasma was collected from an aliquot of the blood sample. 100 microliters of blood and 50 microliters of plasma were applied on Port 1 of an anti-HIV assay strip. 50 microliter of buffer was added onto Port 1 two minutes after blood sample was applied. After about 20 minutes incubation time, the ReLIA instrument scanned and read the densities generated by the capture bands. The CV % of S/CO was 7.8%.

All of these aspects of the invention can be practiced separately or in combination. Further, although preferred embodiments of the subject invention have been described in some detail, it is understood that obvious variations can be made without departing from the spirit and the scope of the invention.

What is claimed is:

1. A test strip comprising
   (a) a first membrane comprising a chromatographic strip having a reaction region, a first position, a second position and a third position;
   (b) a first sample filter at the first position and having an upper surface and a lower surface, wherein the lower surface of the sample filter is in capillary contact with the chromatographic strip;

(c) a conjugate pad at the second position and having an upper surface and a lower surface, wherein the lower surface of the conjugate pad is in capillary contact with the chromatographic strip; and (d) an absorbent pad at the third position wherein the absorbent pad is in capillary contact with the chromatographic strip when a sample is added to the sample filter, wherein the sample filter is capable of separating cells in the sample from fluid in the sample and allows the fluid to pass through to the chromatographic strip, wherein the first and second positions are on opposite sides of the reaction region, wherein the test strip facilitates lateral flow of fluid from the sample filter towards the reaction region and from the conjugate pad towards the reaction region, and wherein (i) the first position and the third position are on opposite sides of the second position, or (ii) the second position and the third position are on opposite sides of the first position.

2. The test strip of claim 1, wherein the sample filter comprises pores of varying sizes and wherein cells in the sample are retained by the sample filter and fluid in the sample passes through the sample filter.

3. The test strip of claim 2, wherein the sample filter comprises first pores having a first pore size and second pores having a second pore size, wherein the first pores are larger than the second pores and further wherein the first pores are closer to the upper surface of the sample filter and the second pores are closer to the lower surface of the sample filter.

4. The test strip of claim 1, further comprising one or more filters or membranes positioned between the sample filter and the chromatographic strip.

5. The test strip of claim 1, further comprising
(e) a reagent pad comprising an upper surface and a lower surface, wherein the lower surface of the reagent pad is in capillary contact with the upper surface of the conjugate pad.

6. The test strip of claim 5, wherein the reagent pad further comprises a reagent.

7. The test strip of claim 6, wherein the reagent is a buffer.

8. The test strip of claim 1, wherein the conjugate pad comprises a conjugate that can be released from the conjugate pad upon application of fluid to the conjugate pad, wherein the conjugate is capable of combining with an analyte to be detected to form a detectable signal.

9. The test strip of claim 1, wherein the reaction region comprises a first binding agent that is capable of binding to an analyte.

10. The test strip of claim 9, wherein the first binding agent is an antibody or antigen.

11. The test strip of claim 9, wherein the conjugate pad comprises a conjugate, and wherein the conjugate comprises a second binding agent.

12. The test strip of claim 11, wherein the second binding agent comprises a detectable marker that binds either to the first binding agent or to the analyte.

13. The test strip of claim 12, wherein the detectable marker is quantifiable.

14. The test strip of claim 8, wherein the conjugate flows from the conjugate pad to come into contact with the fluid from the sample and forms an immobilized complex.

15. The test strip of claim 5, wherein the reagent pad is a second sample filter, and the flow of fluid from the second sample filter to the conjugate pad releases a conjugate from the conjugate pad, wherein the conjugate is capable of combining with an analyte to be detected to form a detectable signal.

16. The test strip of claim 1, wherein the chromatographic strip further comprises an adhesive layer and a backing for the adhesive layer.

17. The test strip of claim 1, wherein the membrane comprises nitrocellulose.

18. The test strip of claim 1, wherein the sample filter is a blood cell/plasma separation membrane.

19. The test strip of claim 1, wherein the sample comprises fluid and cells.

20. The test strip of claim 1, wherein the sample is a blood sample, a saliva sample, a urine sample, sample taken from lymphatic tissues, a sample from a spinal tap, or a sample taken from a peritoneal cavity, synovial fluid from a joint, or fluid from lungs.

21. The test strip of claim 1, wherein the sample comprises red blood cells.

22. The test strip of claim 1, wherein the sample filter comprises a hydrophilic surface that contacts the sample.

23. The test strip of claim 1, wherein the sample filter comprises an S/G membrane.

24. The test strip of claim 3, wherein the sample filter is composed of one or more hydrophobic materials.

25. A test strip comprising
(a) a chromatographic strip having a reaction region, a first position and second position;
(b) a selective membrane;
(c) a sample filter at the first position and having an upper surface and lower surface;
(d) a conjugate pad at the second position and having an upper surface and a lower surface, wherein the lower surface of the conjugate pad is in capillary contact with the chromatographic strip; and
(e) an absorbent pad at a third position,
wherein the absorbent pad is in capillary contact with the chromatographic strip when a sample is added to the sample filter, wherein the sample filter is capable of separating cells in the sample from fluid in the sample and allows the fluid to pass through to the chromatographic strip, wherein the first and second positions are on opposite sides of the reaction region, wherein the selective membrane is in capillary contact with the sample filter and the chromatographic strip, wherein the test strip facilitates lateral flow of fluid from the selective membrane towards the reaction region and from the conjugate pad towards the reaction region, and wherein (i) the first position and the third position are on opposite sides of the second position, or (ii) the second position and the third position are on opposite sides of the first position.

26. A test strip comprising:
(a) a chromatographic strip having a reaction region;
(b) a sample filter having an upper surface and lower surface;
(c) a sample pad in capillary contact with the chromatographic strip and the lower surface of the sample filter;
(d) a conjugate pad having an upper surface and a lower surface, wherein the lower surface of the conjugate pad is in capillary contact with the chromatographic strip; and
(e) an absorbent pad,
wherein the absorbent pad is in capillary contact with the chromatographic strip when a sample is added to the sample filter, wherein the sample filter is capable of separating cells in the sample from fluid in the sample and allows the fluid to pass through to the chromatographic strip, wherein the conjugate pad and the sample pad are on opposite sides of the reaction region, wherein the test strip facilitates lateral flow of fluid from the sample pad towards the reaction region, and wherein (i) the sample filter and the absorbent pad are on opposite sides of the conjugate pad, or (ii) the conjugate pad and the absorbent pad are on opposite sides of the sample filter.

27. A test strip comprising:
(a) a chromatographic strip having a reaction region, a first position and second position;
(b) a sample filter at the first position and having an upper surface and lower surface;
(c) a sample pad having an upper surface and a lower surface, wherein the sample pad is in capillary contact with the chromatographic strip and the upper surface of the sample pad is in capillary contact with the lower surface of the sample filter;
(d) a conjugate pad at the second position and having an upper surface and a lower surface, wherein the lower surface of the conjugate pad is in capillary contact with the chromatographic strip; and
(e) an absorbent pad at a third position,
wherein the absorbent pad is in capillary contact with the chromatographic strip when a sample is added to the sample filter, wherein the sample filter is capable of separating cells in the sample from fluid in the sample and allows the fluid to pass through to the chromatographic strip, wherein the first and second positions are on opposite sides of the reaction region, wherein the test strip facilitates lateral flow of fluid from the sample pad towards the reaction region and from the conjugate pad towards the reaction region, and wherein (i) the first position and the third position are on opposite sides of the second position, or (ii) the second position and the third position are on opposite sides of the first position.

28. The test strip of claim 27, wherein the lower surface of the sample pad is in capillary contact with the chromatography strip.

29. A test strip comprising
(a) a chromatographic strip having a reaction region, a first position and second position;
(b) a sample filter at the first position and having an upper surface and lower surface;
(c) a selective membrane and a sample pad, wherein the selective membrane is either:
(i) in capillary contact with the sample filter and the sample pad, or
(ii) in capillary contact with the sample pad and the chromatographic strip;
and wherein the sample pad has an upper surface and a lower surface, wherein the sample pad is
(i) in capillary contact with the chromatographic strip if the selective membrane is in capillary contact with the sample filter and the sample pad, or
(ii) in capillary contact with the lower surface of the sample filter if the selective membrane is in capillary contact with the sample pad and the chromatographic strip;
(d) a conjugate pad at the second position and having an upper surface and a lower surface, wherein the lower surface of the conjugate pad is in capillary contact with the chromatographic strip; and
(e) an absorbent pad at a third position,
wherein the absorbent pad is in capillary contact with the chromatographic strip when a sample is added to the sample filter, wherein the sample filter is capable of separating cells in the sample from fluid in the sample and allows the fluid to pass through to the chromatographic strip, wherein the first and second positions are on opposite sides of the reaction region, wherein the test strip facilitates lateral flow of fluid from the first position towards the reaction region and from the conjugate pad towards the reaction region, and wherein (i) the first position and the third position are on opposite sides of the second position, or (ii) the second position and the third position are on opposite sides of the first position.

30. The test strip of claim 29, wherein the selective membrane is positioned under the sample filter.

31. The test strip of claim 29, wherein the selective membrane contains an agent that selectively binds to a component in the sample and removes the component from the assay environment.

32. The test strip of claim 31, wherein the agent is selected from the group consisting of an antibody, an antigen, a metabolite, a hormone, an enzyme, a virus, a prion, or parts thereof, and an agent that binds to such.

* * * * *